United States Patent
McGuire, Jr.

(10) Patent No.: US 10,639,118 B2
(45) Date of Patent: May 5, 2020

(54) SURGICAL INCISE DRAPES AND METHODS FOR THEIR APPLICATION

(75) Inventor: James E. McGuire, Jr., Palm Beach, FL (US)

(73) Assignee: entrotech life sciences, inc., San Francisco, CA (US)

(*) Notice: Subject to any disclaimer, the term of this patent is extended or adjusted under 35 U.S.C. 154(b) by 0 days.

(21) Appl. No.: 13/081,021

(22) Filed: Apr. 6, 2011

(65) Prior Publication Data
US 2012/0255562 A1    Oct. 11, 2012

(51) Int. Cl.
*A61B 46/00* (2016.01)
*A61B 46/20* (2016.01)
*A61F 13/02* (2006.01)

(52) U.S. Cl.
CPC ........ *A61B 46/00* (2016.02); *A61B 2046/205* (2016.02); *A61F 13/023* (2013.01); *A61F 13/024* (2013.01)

(58) Field of Classification Search
CPC .. A61F 13/023; A61F 13/024; A61F 13/0253; A61F 13/0236; A61F 13/0243; A61F 13/0259; A61F 13/0263; A61F 13/0266; A61F 13/00–00085; A61F 13/06–069; A61F 13/10–148; A61F 2013/00089–00357; A61F 15/00; A61F 15/005; A61F 13/02–0293; A61B 19/08; A61B 19/088; A61B 2019/084; A61B 2019/085; A61B 46/20; A61B 46/30;
(Continued)

(56) References Cited

U.S. PATENT DOCUMENTS 3,916,887 A * 11/1975 Kelly ..................... A61B 46/00
                                                               128/851
3,934,582 A    1/1976 Gorrie
(Continued)

FOREIGN PATENT DOCUMENTS

EP    0 051 935         5/1982
EP    0 066 899 A2    12/1982
(Continued)

OTHER PUBLICATIONS

Smith & Nephew, OpSite Incise Drape—Sterile, http://www.smith-nephew.com/new-zealand/healthcare/products/product-types/incise-drapes/opsite--incise-drape---sterile/.*
(Continued)

*Primary Examiner* — Keri J Nelson
*Assistant Examiner* — Michelle J Lee
(74) *Attorney, Agent, or Firm* — The Griffith Law Firm, A P.C.; Lisa M. Griffith (57) ABSTRACT

A surgical incise drape of the invention comprises: an essentially transparent or translucent extensible film having opposite first and second major surfaces and opposite first and second side edges; a pressure-sensitive adhesive adhered to at least a major portion of the first major surface of the extensible film; an extensible carrier removably adhered to the second major surface of the extensible film and extending past the first and second side edges of the extensible film to provide gripping portions for facilitating wrinkle-free application of the drape to a patient; and, optionally, a release liner adhered to the pressure-sensitive adhesive opposite the extensible film. Methods of applying such surgical incise drapes to a surgical site on a patient's body are also disclosed.

21 Claims, 5 Drawing Sheets

(58) Field of Classification Search
CPC ........ A61B 2046/205; A61B 46/00–40; A61L 15/00; A61L 15/07; A61L 15/16
USPC ....... 128/849–856; 602/54, 57; 523/105, 111
See application file for complete search history.

(56) References Cited

U.S. PATENT DOCUMENTS

| | | | |
|---|---|---|---|
| 4,524,767 A | 6/1985 | Glassman | |
| 4,745,915 A | 5/1988 | Enright et al. | |
| 4,832,008 A * | 5/1989 | Gilman | A61F 13/023 206/440 |
| 5,000,172 A * | 3/1991 | Ward | A61F 13/023 128/888 |
| 5,197,493 A * | 3/1993 | Grier-Idris | A61B 46/00 128/849 |
| 5,437,622 A | 8/1995 | Carion | |
| 5,592,952 A | 1/1997 | Bohn | |
| 5,611,356 A | 3/1997 | Rothrum | |
| 5,722,943 A * | 3/1998 | Sessions | 602/57 |
| 5,979,450 A | 11/1999 | Baker et al. | |
| 5,985,395 A * | 11/1999 | Comstock et al. | 428/40.1 |
| 6,350,339 B1 | 2/2002 | Sessions | |
| 6,350,399 B1 | 2/2002 | Sessions | |
| 6,530,376 B1 | 3/2003 | Padget et al. | |
| 6,685,682 B1 | 2/2004 | Heinecke et al. | |
| 6,742,522 B1 * | 6/2004 | Baker | A61B 46/10 128/849 |
| 7,704,602 B2 | 4/2010 | Wang et al. | |
| 2002/0000232 A1 * | 1/2002 | Levitt et al. | 128/853 |
| 2005/0013957 A1 * | 1/2005 | Leschinsky | B32B 7/06 428/40.1 |
| 2006/0058721 A1 * | 3/2006 | Lebner | A61F 13/023 602/42 |
| 2009/0105670 A1 * | 4/2009 | Bentley | A61M 1/0088 604/290 |
| 2010/0318013 A1 * | 12/2010 | Fabo et al. | 602/54 |
| 2011/0313048 A1 | 12/2011 | Yang et al. | |
| 2012/0215073 A1 * | 8/2012 | Sherman | A61B 90/30 600/249 |
| 2016/0317358 A1 | 11/2016 | Holm et al. | |

FOREIGN PATENT DOCUMENTS

| | | |
|---|---|---|
| EP | 0 568 401 | 11/1993 |
| EP | 2508146 | 10/2012 |
| WO | WO-97/07760 | 3/1997 |

OTHER PUBLICATIONS

Polymer Properties Database, EVA Films, 2019, http://polymerdatabase.com/Films/EVA%20Films.html (Year: 2019).*

"3M™ Incise Drapes: A Barrier to Bacterial Contamination, New Improved IOBAN Delivery System", GX750; 3M Health Care Limited (2005).

"Superior Surgical Drape Tape and Incise Film Solutions You Can Rely On," Avery Dennison Medical Products (2010).

Penwick, Roger C., "Preoperative Patient Preparation," http://cal.vet.upenn.edu/projects/saortho/chapter_09/09mast.htm, pp. 1-21 (Oct. 13, 2010).

* cited by examiner

SURGICAL INCISE DRAPES AND METHODS FOR THEIR APPLICATION

BACKGROUND OF THE INVENTION

Many types of surgical drapes are known. Some include an adhesive layer for adhering the surgical drape to a patient's skin or other surface. One such drape is an incise drape. An "incise drape" is one where a surgical incision is made directly through the drape and into a patient. By definition, a skin surface covered by a sterile incise drape is bacteria-free (i.e., sterilized) at the beginning of a surgical procedure. Ideally, the skin surface remains bacteria-free during the procedure, resisting the transfer of bacteria from, for example, gloves, instruments, and sponges that may come in contact with, not only the surgical wound, but also the surrounding skin. A drape's barrier and antimicrobial properties are typically effective only so long as the drape is securely attached to the skin.

As described in U.S. Pat. No. 6,742,522, many of today's surgical procedures involve the use of a surgical incise drape. The incise material is usually a clear polymeric film with an adhesive on one side that is covered with a release liner. Two known suppliers of incise materials are Minnesota Mining and Manufacturing Co. and T. J. Smith and Nephew Ltd. Typically, incise material is used in connection with towels or surgical drapes to maintain the surgical area as clean and sterile as possible in order to help reduce the risk of infection. Once the surgical area of the patient has been cleaned and treated with an antimicrobial, the surgical site is squared-off by the use of sterile towels and a surgical drape that has a fenestration (i.e., a specifically designed shape and opening formed therein) of a size that is larger than the expected size of the incision. An incise material is then used to cover all or a portion of the patient's skin left exposed by the towels or the fenestration in the surgical drape or main sheet.

One purpose for using the incise material is to help reduce the migration of germs and bacteria into the incision site. This reduction is needed because, despite cleansing of the skin, the pores still contain additional germs and bacteria. Such germs and bacteria can migrate to the surface as the skin is moved and worked during the course of the surgical procedure. By covering the skin with incise material, however, a lower incidence of surgical site contamination occurs.

Incise drapes typically come in sizes as small as 13×18 centimeters (5×7 inches), but are usually 40×30 centimeters (16×12 inches) through 90×120 centimeters (36×48 inches) and larger. Conventional surgical drapes usually consist of an antimicrobial film incise material covered by a one-piece silicone-coated paper release liner having equal dimensions to the film so that the adhesive is protected. Typical practice is for two people to stand on opposite sides of the operating table with sterile gloved hands, each within the sterile field. One person grips the handle portion of the drape (e.g., a 10- to 15-centimeter film margin that is free of adhesive), while the other person takes the release liner and pulls it away from the underside, exposing the adhesive. The drape is then applied to the patient at the surgical site and subsequently smoothed out and pressed onto the patient with a sterile towel. With larger drapes, this might require three or more people.

Current incise drapes are usually large and cumbersome to apply to the patient without wrinkles and without the drape sticking to itself in the process. As described above, drape application usually requires at least two or three people, creating a drain on operating room personnel and contributing to rising hospital costs. Applying conventional incise drapes can be a frustrating experience, even for those skilled in the art of applying these drapes. Surgical incise drapes are typically flimsy (so as to be very conformable to the contours of the skin) and include an aggressive pressure-sensitive adhesive for adhesion to the skin. These two characteristics, when combined with the large size of many incise drapes, frequently results in the application of a wrinkled drape.

For proper functioning of a surgical incise drape, it is important that the incise drape be wrinkle-free after it is applied, especially directly at the incision point in order for the surgeon to be able to make a clean surgical incision. Wrinkles in the drape make it difficult for the surgeon to see through to the skin (i.e., translucency and visibility are important). Furthermore, if the incise drape includes wrinkles, the incise drape may not prevent bacteria on the skin from getting into the wound. Maintaining a sterile surface at the point of incision helps prevent surgical wound infections.

In an attempt to address this important consideration, U.S. Pat. No. 6,742,522 discloses the use of a film handle at a leading edge of a flexible film used as the backing of a surgical incise drape. The film handle is preferably formed of a relatively stiff material as compared to the flexible film. Although the configurations described therein purportedly lead to wrinkle-free application of the surgical incise drapes, the methodology for such application is complicated.

The importance of an incise drape being wrinkle-free after it is applied, especially directly at the incision point in order for the surgeon to be able to make a clean surgical incision, is also discussed in U.S. Pat. No. 5,985,395. Indeed, there is a need for improved surgical incise drapes and methods of applying such drapes to a patient.

While a carrier has been used to apply certain medical laminates to a patient's skin, those applications are limited. For example, U.S. Pat. No. 6,350,339 discloses a non-stretchable wound dressing having a flexible, non-stretching cover sheet having adhesive on one side thereof and having two spaced strip-form gripping tabs at opposite ends thereof. The cover sheet covers a urethane wound dressing with the adhesive of the cover sheet being in contact with the urethane and the urethane having an adhesive layer on an opposite side thereof. For storage and prior to application to a patient, the adhesive of the urethane wound dressing is in contact with a releasable surface of a carrier, such as cardboard. For application to a patient, one of the cover sheet gripping tabs is pulled so as to release the cover sheet and wound dressing from the carrier, the cover sheet preventing stretching of the wound dressing. The combination is then applied to a patient, again the cover sheet preventing stretching of the wound dressing. The other gripping tab of the cover sheet is then pulled to separate the cover sheet from the wound dressing, leaving the wound dressing on the patient with no stretching thereof.

Further, a flexible but non-stretching backing for a urethane wound dressing is disclosed in European Patent Publication No. EP 0 066 899 A2, which is directed toward a delivery system for adhesively affixed copolymer medical coverings such as adhesive bandages, surgical drapes, medical dressings and the like. The delivery system includes a film sheet disposed on and supported by a film sheet carrier. The carrier remains in contact with the wound dressing using an adhesive while the dressing is being applied to the patient and is separated from the wound dressing only after the dressing has been placed on the patient, thereby eliminating stretching during application of the dressing. A carrier removal tab is affixed to the back of the film sheet carrier to facilitate its separation from the film sheet after affixation of the film sheet to the subject. The carrier is described as being relatively un-stretchable and rigid as compared to the film sheet. The carrier is also described as being bendable to conform generally to the contours of the part of the biological subject for supporting the film sheet until after the film sheet is affixed to cover the selected part of the biological subject. The only material described for the carrier therein is a polyester film sold by E.I. du Pont de Nemours of Wilmington, Del. under the trade designation, MYLAR. As described in the background discussion of U.S. Pat. No. 6,350,339, however, MYLAR does not possess the flexibility desired in a material suitable for the application of a flexible wound cover contouring agent.

Despite various attempts to provide surgical incise drapes that are easy to apply effectively, improvements are needed in that regard. Importantly, conformability to a patient's individual body features, without sacrificing ease of application, is in need of improvement for maximizing effectiveness of surgical incise drapes in warding off harmful bacteria.

BRIEF SUMMARY OF THE INVENTION

A surgical incise drape of the invention comprises: an essentially transparent or translucent extensible film having opposite first and second major surfaces and opposite first and second side edges; a pressure-sensitive adhesive adhered to at least a major portion of the first major surface of the extensible film; an extensible carrier removably adhered to the second major surface of the extensible film and extending past the first and second side edges of the extensible film to provide gripping portions for facilitating wrinkle-free application of the drape to a patient; and, optionally, a release liner adhered to the pressure-sensitive adhesive opposite the extensible film. According to an exemplary embodiment of the invention, the surgical incise drape comprises a release liner.

According to one aspect of the invention, the extensible carrier has a thickness of at least about 15 μm. According to another aspect of the invention, the extensible carrier has a thickness of at least about 50 μm. According to another aspect of the invention, the extensible carrier comprises a material having at least about 10% elongation when tested according to ASTM D412. In a further embodiment, the extensible carrier comprises a material having at least about 25% elongation when tested according to ASTM D412. In a yet further embodiment, the extensible carrier comprises a material having at least about 50% elongation when tested according to ASTM D412. According to another aspect of the invention, the extensible carrier is essentially transparent or translucent. An exemplary extensible carrier comprises a polyolefin.

An exemplary extensible film is polyurethane-based. According to one aspect of the invention, the extensible film comprises a material having at least about 10% elongation when tested according to according to ASTM D412. In a further embodiment, the extensible film comprises a material having at least about 25% elongation when tested according to according to ASTM D412. In a yet further embodiment, the extensible film comprises a material having at least about 50% elongation when tested according to ASTM D412.

According to yet another aspect of the invention, the surgical incise drape comprises at least one rigid tab positioned along each of opposite sides of the surgical incise drape. In an exemplary embodiment, each rigid tab is positioned between the pressure-sensitive adhesive and the optional release liner. In one embodiment, the rigid tabs extend substantially the entire length of the opposite sides of the surgical incise drapes. In another embodiment, a series of spaced-apart rigid tabs is positioned on opposite sides of the surgical incise drape. In another exemplary embodiment, the rigid tabs are opaque. In yet another exemplary embodiment, the rigid tabs further comprise an outwardly exposed adhesive.

A method of applying a surgical incise drape to a surgical site on a patient's body comprises steps of: providing a surgical incise drape of the invention; optionally, disinfecting the surgical site on the patient's body; optionally, removing the optional release liner from the surgical incise drape; firmly gripping the extensible carrier on the gripping portions adjacent first and second side edges of the extensible film; positioning the surgical incise drape over the surgical site on the patient's body with the pressure-sensitive adhesive directed toward the surgical site on the patient's body; applying pressure to the extensible carrier along the surgical incise drape beginning at a point where a surgical incision is to be made on the patient's body; and conformably adhering the surgical incise drape over the patient's body using the gripping portions. In one embodiment, the method further comprises the step of removing the extensible carrier from the extensible film after the surgical incise drape is adequately adhered to the surgical site on the patient's body.

DETAILED DESCRIPTION OF THE INVENTION

Improved surgical incise drapes and methods of their application are provided. Surgical incise drapes of the invention comprise: an essentially transparent or translucent extensible film having opposite first and second major surfaces and opposite first and second side edges; a pressure-sensitive adhesive adhered to at least a major portion of the first major surface of the extensible film; an extensible carrier removably adhered to the second major surface of the extensible film and extending past the first and second side edges of the extensible film to provide a gripping portion for facilitating wrinkle-free application of the drape to a patient; and, optionally, a release liner adhered to the pressure-sensitive adhesive opposite the extensible film. The surgical incise drape and extensible carrier are also to be understood as having first and second side edges along the same sides as first and second side edges of the extensible film.

Surgical incise drapes of the invention have improved conformability to facilitate effective adherence of the drapes to a patient's individual body features, without sacrificing ease of handling during application. To facilitate conformability of the surgical incise drape during application, particularly when applying the drape to a relatively large and uneven area on a patient's body, an extensible film as well as an extensible carrier are used therein. The extensible film and the extensible carrier are laminated together to provide a surgical incise drape with improved handling capabilities for wrinkle-free adherence thereof to a patient's body at the site of a medical procedure where a surgical incision is to be made. By utilizing an extensible carrier, surgical incise drapes of the invention have improved handling capabilities over such large and uneven surfaces as compared to conventional wound dressings and the like that utilize relatively rigid carriers for their application to typically smaller and more even surfaces on a patient's body, where conformability is not as major of a concern.

The terms "extensible" and "extensibility" refer to a material's ductility and its ability to be stretched and recover to essentially its original state after stretching. Extensibility is evident when elongating (also referred to as stretching) the material by at least about 10%, preferably at least about 25%. In one embodiment, an extensible material according to the invention imparts recovery (i.e., initial length of the sample divided by length of the relaxed sample) of greater than 90% when a sample of such is stretched 10%, 25%, 50%, 100%, 150%, or even more of its initial length according to ASTM D412. In another embodiment, an extensible material according to the invention imparts recovery of at least about 95% when tested as such. In yet a further embodiment, an extensible material according to the invention imparts recovery of at least about 99% when so tested. In still a further embodiment, an extensible material according to the invention imparts about 100% recovery when so tested.

Preferably, extensible materials are capable of recovering to their original state when stretched (i.e., elongated) up to about 125% of their initial length or more. More preferably, extensible materials according to the invention are capable of recovering to their original state when stretched up to about 150% of their initial length or more. According to one aspect of the invention, extensible materials are capable of elongating more than 200% before breaking. Further preferable are extensible materials that exhibit essentially no plastic deformation when stretched up to about 150% of their initial length.

According to an exemplary aspect of the invention, extensible materials of the invention exhibit greater than about 210% elongation at break when tested according to ASTM D412. In a further exemplary embodiment, extensible materials of the invention exhibit greater than about 260% elongation at break when tested according to ASTM D412. In a still further exemplary embodiment, extensible materials of the invention exhibit greater than about 300% elongation at break when tested according to ASTM D412. In a further exemplary embodiment still, extensible materials of the invention exhibit greater than about 350% elongation at break when tested according to ASTM D412.

According to another exemplary aspect of the invention, extensible materials of the invention exhibit less than about 3% deformation after 25% elongation when tested according to ASTM D412. In a further exemplary embodiment, extensible materials of the invention exhibit less than about 2% deformation after 25% elongation when tested according to ASTM D412. In a still further exemplary embodiment, extensible materials of the invention exhibit less than about 1% deformation after 25% elongation when tested according to ASTM D412.

According to another aspect of the invention, exemplary extensible materials of the invention exhibit less than about 8% deformation after 50% elongation when tested according to ASTM D412. In a further exemplary embodiment, extensible materials of the invention exhibit less than about 5% deformation after 50% elongation when tested according to ASTM D412. In a still further exemplary embodiment, extensible materials of the invention exhibit less than about 2% deformation after 50% elongation when tested according to ASTM D412.

According to another exemplary aspect of the invention, extensible materials of the invention require a force of less than about 40 Newtons to elongate the material to 150% its initial length. In a further exemplary embodiment, extensible materials of the invention require a force of less than about 30 Newtons to elongate the material to 150% its initial length. In yet a further exemplary embodiment, extensible materials of the invention require a force of less than about 20 Newtons to elongate the material to 150% its initial length.

Extensible Film

In one embodiment, extensible films according to the invention are essentially transparent. Transparency of the extensible film facilitates placement of the drape on a patient's body, as well as precise positioning of a surgical incision therethrough during a medical procedure. The extensible film is essentially transparent in order to facilitate at least one of these considerations. In another embodiment, extensible films according to the invention are essentially translucent, which also facilitates placement of the drape on a patient's body and surgical incisions therethrough.

Any suitable material can be used for the extensible film. For example, the extensible film can comprise as its base polymer a polyvinyl fluoride, a polyacrylate, a polyolefin, a polyurethane, a silicone polymer, modified (e.g., hybrid) polymers thereof, a polyester, a polyamide, or others known to those of ordinary skill in the art and combinations thereof. In an exemplary embodiment, the extensible film is polyurethane-based. Polyurethane-based extensible films can include any suitable polyurethanes, such as polycarbonate-based polyurethanes.

Any suitable additives can be present in conjunction with the base polymer as known to those skilled in the art. In an exemplary embodiment, extensible films of the invention comprise an essentially uncrosslinked extensible material. While the use of certain amounts of crosslinker may still allow formation of extensible films of the invention, if crosslinkers are present, they are generally used in an amount of less than about 4 parts by weight, and preferably less than about 2 parts by weight, based on 100 parts by weight of any polymer crosslinkable therewith prior to any crosslinking reaction. Further, crosslinkers may be present if they are not used in combination with polymers that are crosslinkable therewith or where, if crosslinkable, resulting crosslink density is minimal (e.g., due to minimal reactive sites on the base polymer) so as not to significantly affect extensibility of the film. In a preferred embodiment, the extensible film is essentially free of crosslinkers and reaction products thereof. As such, crosslinkers and reaction products are not discernible when using chemical analysis.

The extensible film has opposite first and second major surfaces and opposite first and second side edges. The extensible film comprises any suitable thickness. Advantageously, however, thickness of the extensible film can be less than that required in conventional incise drapes due to its application in combination with the extensible carrier of the present invention. In one embodiment, the extensible film has a thickness of about 1 micron to about 125 microns, or more specifically about 3 microns to about 95 microns. In an exemplary embodiment, the extensible film has a thickness of about 20 microns or less, more specifically about 5 microns to about 15 microns.

According to one aspect of the invention, an extensible film of the desired thickness is formed using dispersion chemistry. Dispersion chemistry is well known to those skilled in the art. While the % solids will vary, in one embodiment, a dispersion having about 10-15% solids was found useful for formation of the extensible film using methodology known to those of ordinary skill in the art. As formed, the extensible film has opposite first and second major surfaces and opposite first and second side edges as referenced herein.

Pressure-Sensitive Adhesive

A pressure-sensitive adhesive is formed on at least a portion of the first major surface of the extensible film for removable attachment of an incise drape comprising the same on a patient's body during a medical procedure. While the entire first major surface of the extensible film need not be covered with a pressure-sensitive adhesive, at least a major portion thereof is generally coated with a pressure-sensitive adhesive in order to facilitate effective adherence of the extensible film to a patient's body. Uniform attachment of the extensible film proximate a surgical incision site helps to maintain a sterile surgical field.

Any suitable pressure-sensitive adhesive may be used as known to those of ordinary skill in the art. Preferably, the pressure-sensitive adhesive is sufficiently tacky at body temperature to aggressively, yet removably, adhere the extensible film to a patient's body. Aggressive adhesives are preferred due to the stress that the extensible film is under during surgery as a result of retraction of the incision, the warm and moist environment, and the abrasion encountered by the extensible film from the surgeon's hands and instruments moving in and out of the incision. An exemplary pressure-sensitive adhesive comprises an antimicrobial pressure-sensitive adhesive. For example, such antimicrobial pressure-sensitive adhesives comprise those adhesives described in PCT Patent Publication No. WO2010/080936, entitled "Chlorhexidine-Containing Antimicrobial Laminates."

The pressure-sensitive adhesive is formed on the first major surface of the extensible film as a pressure-sensitive adhesive layer. The pressure-sensitive adhesive layer comprises any suitable thickness. For example, in one embodiment, the pressure-sensitive adhesive layer has a thickness of about 5 microns to about 150 microns. In an exemplary embodiment, the pressure-sensitive adhesive layer has a thickness of about 25 microns.

Extensible Carrier

Extensible carriers used according to the invention are removably adhered to the second major surface of the extensible film. Extensible carriers in surgical incise drapes of the invention extend past the first and second side edges of the extensible film to provide a gripping portion for facilitating wrinkle-free application of the drape to a patient.

Any suitable material can be used for the extensible carrier. For example, the extensible carrier can comprise as its base polymer a polyvinyl fluoride, a polyolefin, a polyacrylate, a polyurethane, a silicone polymer, modified (e.g., hybrid) polymers thereof, a polyester, a polyamide, or others known to those of ordinary skill in the art and combinations thereof. In an exemplary embodiment, the extensible carrier comprises a polyolefin due to, for example, cost considerations.

In one embodiment, extensible carriers according to the invention are essentially transparent. In another embodiment, extensible carriers according to the invention are essentially translucent. Transparency and translucency of the extensible carrier facilitates placement of the drape on a patient's body, particularly when used in combination with an essentially transparent or translucent extensible film.

Any suitable additives can be present in conjunction with the base polymer as known to those skilled in the art. In an exemplary embodiment, extensible carriers of the invention comprise an essentially uncrosslinked extensible material. While the use of certain amounts of crosslinker may still allow formation of extensible carriers of the invention, if crosslinkers are present, they are generally used in an amount of less than about 4 parts by weight, and preferably less than about 2 parts by weight, based on 100 parts by weight of any polymer crosslinkable therewith prior to any crosslinking reaction. Further, crosslinkers may be present if they are not used in combination with polymers that are crosslinkable therewith or where, if crosslinkable, resulting crosslink density is minimal (e.g., due to minimal reactive sites on the base polymer) so as not to significantly affect extensibility of the carrier. In a preferred embodiment, the extensible carrier is essentially free of crosslinkers and reaction products thereof. As such, crosslinkers and reaction products are not discernible when using chemical analysis.

The extensible carrier has any suitable thickness of at least that thickness necessary to support the extensible film during its application on a patient's body. In an exemplary embodiment, the extensible carrier has a thickness of at least about 15 microns. In a further embodiment, the extensible carrier has a thickness of at least about 50 microns. According to another embodiment, the extensible carrier has a thickness up to about 125 microns.

Advantageously, to facilitate ease of effective application of the drape, the extensible carrier is positioned to extend past at least the first and second side edges of the extensible film a suitable distance in order to provide a gripping portion at each edge of the drape for facilitating wrinkle-free application of the drape to a patient. In addition to extending past at least the first and second side edges of the extensible film, the extensible carrier can also extend past other edges of the extensible film. In one embodiment, the extensible carrier extends at least about 0.5 inch (1.3 centimeters) past first and second side edges of the extensible film. In an exemplary embodiment, the extensible carrier extends about 0.5 inch (1.3 centimeters) to about 1.0 inch (2.6 centimeters) past first and second side edges of the extensible film. The amount of the carrier's extension need not be the same past the first and second side edges of the extensible film and can vary along each side, so long as at least one gripping portion exists at opposite edges of the drape.

Preferably, extensibility of the extensible film and the extensible carrier are similar. However, extensible of each of the extensible film and the extensible carrier may vary.

Nonetheless, for ease of application, it is preferred that extensibility of the carrier be at least as great as extensibility of the film.

Any suitable method can be used to removably adhere the extensible carrier to the extensible film. In general, adhesion strength between the extensible film and the extensible carrier is less than adhesion strength between the pressure-sensitive adhesive on the first major surface of the extensible film and the patient's body.

In one embodiment, the extensible carrier is adhered to the extensible film essentially only along its perimeter. In an exemplary embodiment, the extensible carrier is removably adhered to the extensible film at opposite sides of the carrier. That is, the extensible carrier is adhered to the extensible film at first and second side edges of the extensible film. The extensible carrier may be adhered to extensible film using mechanical or chemical mechanisms. For example, the extensible carrier is adhered to the extensible film using a pressure-sensitive adhesive in one embodiment. According to another embodiment, the extensible carrier is adhered to the extensible film without using an adhesive. For example, the extensible carrier may be adhered to the extensible film using electrostatic bonding or similar techniques.

Optional Rigid Tabs

In order to provide enhanced gripping portions for facilitating wrinkle-free application of surgical incise drapes of the invention, at least one rigid tab is provided on at least one layer along each of opposite sides of the surgical incise drape. For example, in one embodiment, at least one rigid tab is provided along each of first and second side edges of the extensible carrier. In another embodiment, at least one rigid tab is provided along each of first and second side edges of the extensible film. In a further embodiment, at least one rigid tab is provided along each of first and second side edges of both laminate layers. Each rigid tab may extend substantially the entire length of the side on which it is positioned or multiple rigid tabs may be positioned along the side in shorter segments—e.g., when a series of spaced-apart rigid tabs is provided. For example, in one embodiment, a series of spaced-apart rigid tabs is provided on first and second side edges of the surgical incise drape.

Placement within the surgical incise drape itself can vary. Along opposite sides of the surgical incise drape, at least one, preferably each, rigid tab is positioned between the extensible film and the extensible carrier in one embodiment. At least one, preferably each, rigid tab is positioned on the extensible carrier on a major surface thereof opposite that surface adhered to the extensible film in another embodiment. At least one, preferably each, rigid tab is positioned between the extensible film and the optional release liner in yet another embodiment. In an exemplary embodiment, each rigid tab is positioned between the first major surface of the extensible film and an optional release liner adhered thereto.

Dimensions of the rigid tabs may vary to provide the gripping portion desired. Importantly, however, dimensions of the rigid tabs are generally such that the rigid tabs are positioned along the perimeter of the surgical incise drape without extending across the central portion thereof. In this manner, the rigid tabs do not interfere with the advantages otherwise obtainable with surgical incise drapes of the present invention. That is, dimensions and placement of the rigid tabs still allows for the extensible film and extensible carrier laminate to cooperatively facilitate conformability of the drape to a patient's body during application of the drape. In one embodiment, the rigid tabs have a width of about 2.5 centimeters (about 1 inch). The rigid tabs are individually positioned such that their outer edges are essentially aligned with the first and second side edges of the extensible film or extensible carrier or they may be individually positioned such that their outer edges are inside or outside the outer surface of the first and second side edges of the extensible film or extensible carrier. In an exemplary embodiment, the rigid tabs are positioned such that the outer surface of the first and second side edges of the extensible film extends along approximately the center of the rigid tabs.

Any suitable material or combinations thereof may be used for the rigid tabs. In general, the rigid tabs are less extensible than extensible carriers of the invention. In one embodiment, the rigid tabs are formed from a polymeric material (e.g., polyethylene terephthalate). Unlike the extensible film and preferred extensible carrier, the rigid tabs need not be essentially transparent or translucent in preferred embodiments. In one embodiment, the rigid tabs are metallized or otherwise made opaque for ease of locating and handling the rigid tabs during application of the surgical incise drape.

Any suitable methodology may be used to securely position the rigid tabs as desired. The rigid tabs may be removably or more permanently secured on the surgical incise drape. For example, the rigid tabs may be removably secured using a pressure-sensitive adhesive or peelable thermal laminate. For example, where the rigid tab is positioned between the extensible film and the release liner, it may be effectively secured using the pressure-sensitive adhesive layer on the first major surface of the extensible film. The rigid tabs may be more permanently secured using thermal bonding, ultrasonic welding, or any of a variety of known permanent bonding methods selected according to the materials being bonded.

In one embodiment, the rigid tabs are secured using a double-sided adhesive tape. In a further aspect of this embodiment, the double-sided adhesive tape comprises an aggressive adhesive, which may comprise, for example, the same chemistry as that of the pressure-sensitive adhesive used elsewhere in the surgical incise drape, but a thicker layer thereof. According to one aspect of this embodiment, where at least one aggressive adhesive surface of the double-sided adhesive tape is outwardly exposed (e.g., when a double-sided adhesive tape is used to securely position the rigid tab between the extensible film and the release liner), the surgical incise drape can be more effectively adhered to towels and surgical drapes along its border after application thereof to a patient's body. Securement of the rigid tabs to the surgical incise drape in this manner, not only serves to securely position the rigid tabs as desired, but it also facilitates improved adherence of the incise drape to surrounding materials.

Adhesive used to secure the rigid tabs may extend across the entire surface of the rigid tab. In one embodiment, however, adhesive outwardly extends approximately halfway across each rigid tab to its centerline, where a perforation exists in the rigid tab. As such, when the rigid tabs are positioned such that the outer surface of the first and second side edges of the extensible film extend along approximately the center of the rigid tabs, the rigid tabs may be broken along the perforation after application of the surgical incise drape and the non-adhesive coated portion of the rigid tabs discarded.

Optional Release Liner

Prior to application of the surgical incise drape, an optional release liner may be adhered to the pressure-sensitive adhesive on a major surface thereof opposite that surface of the pressure-sensitive adhesive on which the extensible film is adhered. Any suitable release liner may be used as known to those of ordinary skill in the art.

Further, the release liner may have any suitable dimensions to protect the pressure-sensitive adhesive until adherence of the surgical incise drape to a patient's body. In one embodiment, the release liner has a width and a length approximately the same as those of the extensible film. In a further embodiment, the optional release liner extends past the first and second side edges of the extensible film to, for example, approximate at least one of width and length of the extensible carrier. Any suitable material may be used for the release liner as known to those of ordinary skill in the art. For application, the release liner is removed as known to those skilled in the art.

Exemplary Surgical Incise Drape Configurations

Figure 1A:
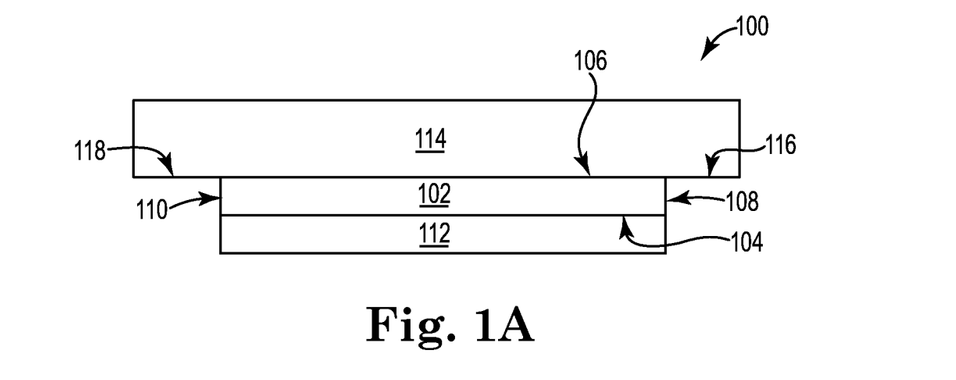
FIG. 1A is a side perspective view of a surgical incise drape of the invention.

In view of the foregoing, FIG. 1A is a side perspective view of one embodiment of a surgical incise drape 100 of the invention. As illustrated therein, an extensible film 102 having opposite first and second major surfaces 104, 106 and opposite first and second side edges 108, 110. A pressure-sensitive adhesive 112 is adhered to at least a major portion of the first major surface 104 of the extensible film 102. An extensible carrier 114 is removably adhered to the second major surface 106 of the extensible film 102 and extends past the first and second side edges 108, 110 of the extensible film 102 to provide a first gripping portion 116 along the first side edge 108 of the extensible film 102 and a second gripping portion 118 along the second side edge 110 of the extensible film 102 for facilitating wrinkle-free application of the drape 100 to a patient.

Figure 1B:
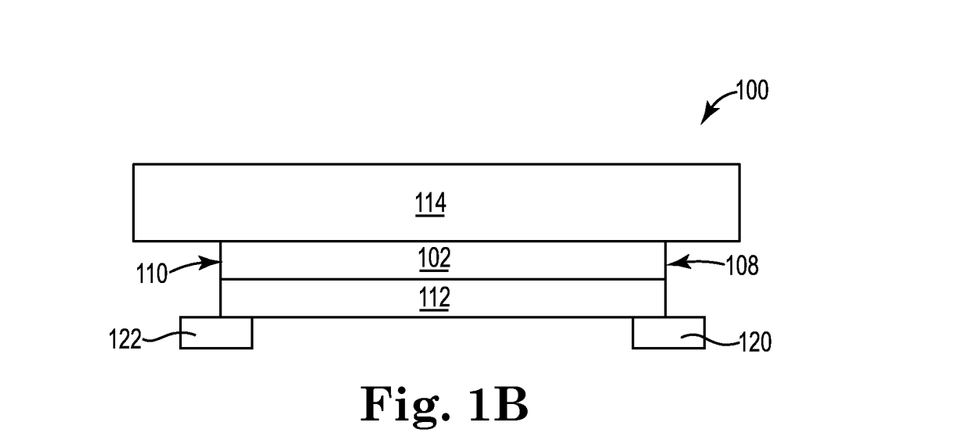
FIG. 1B is a side perspective view of a further embodiment of the surgical incise drape illustrated in FIG. 1A, wherein the drape comprises rigid tabs.

A further embodiment of the surgical incise drape 100 illustrated in FIG. 1A is illustrated in the side perspective view of FIG. 1B. As illustrated therein, a first rigid tab 120 is positioned along the first side edge 108 of the extensible film 102 with the pressure-sensitive adhesive 112 disposed therebetween. A second rigid tab 122 is positioned along the second side edge 110 of the extensible film 102 with the pressure-sensitive adhesive 112 disposed therebetween.

Figure 1C:
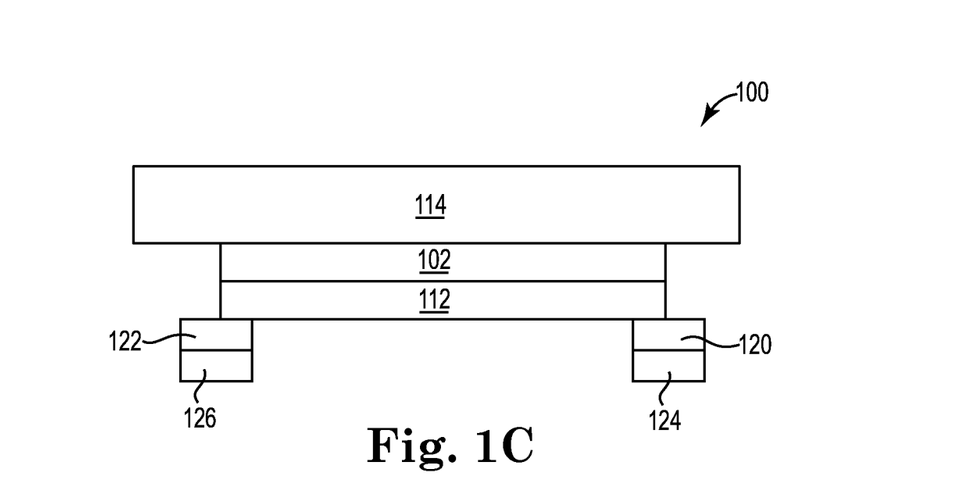
FIG. 1C is a side perspective view of a further embodiment of the surgical incise drape illustrated in FIG. 1B, wherein the rigid tabs comprise an outwardly exposed adhesive.

A further embodiment of the surgical incise drape 100 illustrated in FIG. 1B is illustrated in the side perspective view of FIG. 1C. As illustrated therein, an outwardly exposed adhesive 124 is positioned on the first rigid tab 120 and an outwardly exposed adhesive 126 is positioned on the second rigid tab 122.

Figure 1D:
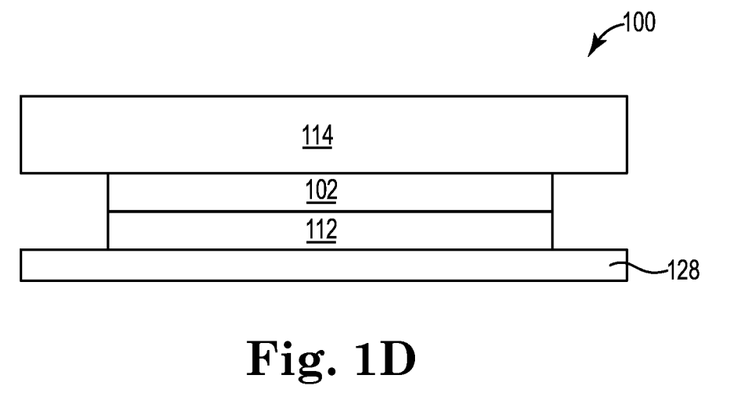
FIG. 1D is a side perspective view of a further embodiment of the surgical incise drape illustrated in FIG. 1A, wherein the drape comprises a release liner.

A further embodiment of the surgical incise drape 100 illustrated in FIG. 1A is illustrated in the side perspective view of FIG. 1D. As illustrated therein, an optional release liner 128 is present and adhered to the pressure-sensitive adhesive 112 opposite the extensible film 102.

Figure 2A:
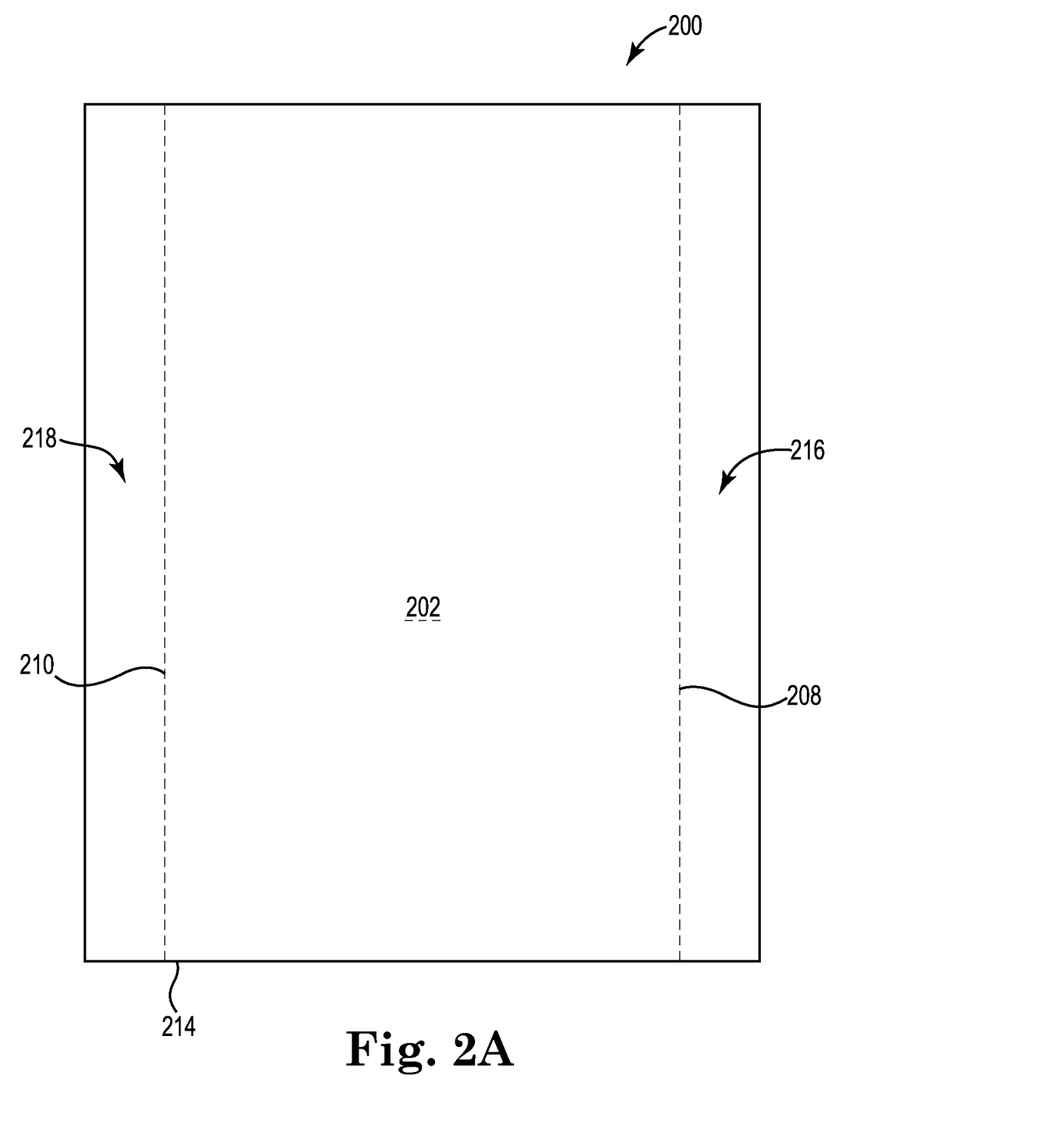
FIG. 2A is a top extensible carrier-side plan view of a surgical incise drape of the invention.

FIG. 2A is a top extensible carrier-side plan view of a surgical incise drape 200 of the invention. As illustrated therein, an extensible film 202 having opposite first and second side edges 208, 210. A pressure-sensitive adhesive (not separately shown) is adhered to at least a major portion of a first major surface of the extensible film 202 and an extensible carrier 214 is removably adhered to a second major surface of the extensible film 202. The extensible carrier 214 extends past the first and second side edges 208, 210 of the extensible film 202 to provide a first gripping portion 216 along the first side edge 208 of the extensible film 202 and a second gripping portion 218 along the second side edge 210 of the extensible film 202 for facilitating wrinkle-free application of the drape 200 to a patient.

Figure 2B:
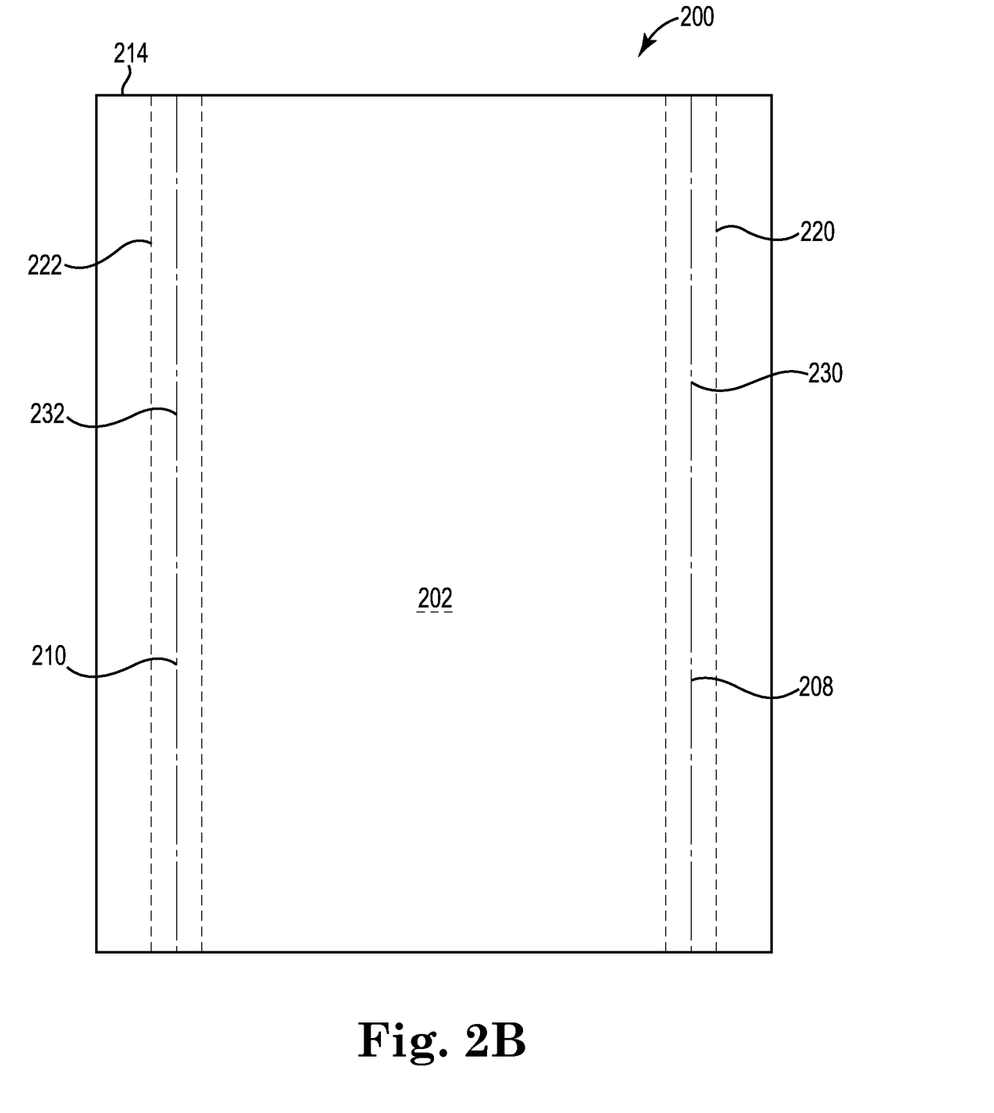
FIG. 2B is a top extensible carrier-side plan view of a further embodiment of the surgical incise drape illustrated in FIG. 2A, wherein the drape comprises rigid tabs.

FIG. 2B is a top extensible carrier-side plan view of a further embodiment of the surgical incise drape 200 illustrated in FIG. 2A, wherein the drape 200 comprises a first rigid tab 220 extending along the first side edge 208 of the extensible film 202 and a second rigid tab 222 extending along the second side edge 210 of the extensible film 202. In this embodiment, each of the rigid tabs 220, 222 is positioned such that the first and second side edges 208, 210 of the extensible film 202 extend along approximately the centerlines 230, 232 of the first and second rigid tabs 220, 222.

Figure 2C:
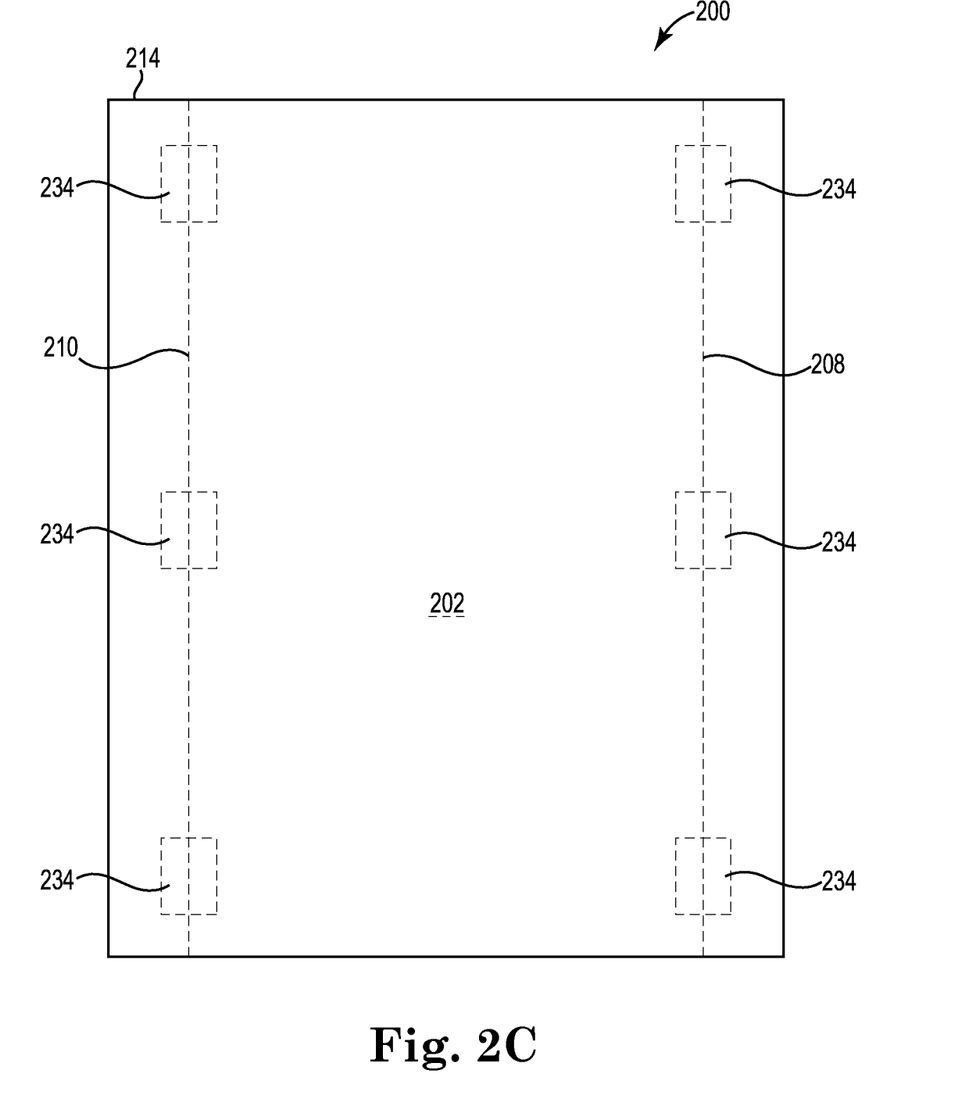
FIG. 2C is a top extensible carrier-side plan view of a further embodiment of the surgical incise drape illustrated in FIG. 2A, wherein the drape comprises multiple rigid tabs.

FIG. 2C is a top extensible carrier-side plan view of a further embodiment of the surgical incise drape 200 illustrated in FIG. 2A, wherein the drape 200 comprises multiple rigid tabs 234 extending along the first and second side edges 208, 210 of the extensible film 202. In this embodiment, each of the rigid tabs 234 is positioned such that the first and second side edges 208, 210 of the extensible film 202 extend along approximately the centerlines (not separately numbered) of the rigid tabs 234.

Method of Applying Surgical Incise Drapes

After its formation, the surgical incise drape is folded or rolled in any suitable manner for packaging prior to delivery. According to an exemplary application method, at least the portion of a patient's body to be covered with the surgical incise drape is disinfected according to procedures known to those of ordinary skill in the art. After any antimicrobial solution dries, the surgical incise drape is generally removed from its packaging and adhered to the patient. If present, the release liner is removed from the surgical incise drape using methodology known to those skilled in the art to simultaneously or sequentially expose the pressure-sensitive adhesive layer.

The extensible carrier is firmly gripped adjacent first and second side edges of the extensible film. If present, preferably, the extensible carrier is gripped simultaneously with at least one rigid tab on each of the opposite edges of the surgical incise drape. The gripped surgical incise drape is then positioned over the portion of the patient's body and, with or without contacting the gripping portion of the surgical incise drape, pressure is then applied to the extensible carrier along the outside of the surgical incise drape beginning at a point where a surgical incision is to be made during a medical procedure. As pressure is applied on the extensible film through the extensible carrier in order to adhere the drape to the patient's body in a wrinkle-free manner, the drape is extended conformably over the patient's body using the gripping portions of the extensible carrier and/or rigid tabs for ease thereof. After the drape is effectively adhered to the patient's body, the extensible carrier is peeled away from the extensible film and, optionally, discarded. If present, adhesive on the rigid tabs is secured to towels and surgical drapes bordering the incise drape for enhanced protection from germs and bacteria. After the medical procedure, the incise drape is removed from the patient's body by gently peeling back the drape at an approximately 180-degree angle from the patient's skin.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

Further, as used throughout, ranges may be used as shorthand for describing each and every value that is within the range. Any value within the range can be selected as the terminus of the range. Similarly, any discrete value within the range can be selected as the minimum or maximum value recited in describing and claiming features of the invention.

The invention claimed is:

1. A surgical incise drape comprising:
   an essentially transparent or translucent extensible film having opposite first and second major surfaces and opposite first and second side edges;
   a pressure-sensitive adhesive adhered to at least a majority of the first major surface of the extensible film;
   an extensible carrier removably adhered to the second major surface of the extensible film and extending past the first and second side edges of the extensible film to provide gripping portions for facilitating wrinkle-free application of the drape to a patient, wherein the extensible carrier continuously extends across the entire second major surface area of the extensible film and is removably adhered to the extensible film at least at the first and second side edges of the extensible film;
   optionally, a release liner adhered to the pressure-sensitive adhesive opposite the extensible film; and
   at least one rigid tab positioned along each of opposite first and second side edges of the surgical incise drape, wherein the rigid tabs further comprise an outwardly exposed adhesive.

2. The surgical incise drape of claim 1, wherein the at least one rigid tab positioned along each of opposite first and second side edges of the surgical incise drape comprises a series of spaced-apart rigid tabs.

3. The surgical incise drape of claim 2, wherein the series of spaced-apart rigid tabs extend substantially the entire length of the opposite first and second side edges of the surgical incise drape.

4. The surgical incise drape of claim 2, wherein the series of spaced-apart rigid tabs are opaque.

5. A method of applying a surgical incise drape to a surgical site on a patient's body, the method comprising steps of:
   providing the surgical incise drape of claim 1;
   optionally, disinfecting the surgical site on the patient's body;
   if present, removing the optional release liner adhered to the pressure-sensitive adhesive;
   gripping the extensible carrier on at least one of the gripping portions and rigid tabs adjacent first and second side edges of the extensible film;
   positioning the surgical incise drape over the surgical site on the patient's body with the pressure-sensitive adhesive directed toward the surgical site on the patient's body;
   applying pressure to the extensible carrier along the surgical incise drape beginning at a point where a surgical incision is to be made on the patient's body; and
   conformably adhering the surgical incise drape over the patient's body using at least one of the gripping portions and rigid tabs.

6. The method of claim 5, further comprising the step of removing the extensible carrier from the extensible film after the surgical incise drape is adhered to the surgical site on the patient's body.

7. The surgical incise drape of claim 1, wherein the extensible carrier has a thickness of at least about 15 µm.

8. The surgical incise drape of claim 1, wherein the extensible carrier comprises a material having at least about 25% elongation when tested according to ASTM D412.

9. The surgical incise drape of claim 1, wherein the extensible carrier comprises a material having at least about 50% elongation when tested according to ASTM D412.

10. The surgical incise drape of claim 1, wherein the extensible carrier comprises a polyolefin.

11. The surgical incise drape of claim 1, wherein the extensible film is polyurethane-based.

12. The surgical incise drape of claim 1, wherein the extensible film comprises a material having at least about 25% elongation when tested according to ASTM D412.

13. The surgical incise drape of claim 1, wherein the extensible film comprises a material having at least about 50% elongation when tested according to ASTM D412.

14. The surgical incise drape of claim 1, wherein the extensible carrier is essentially transparent or translucent.

15. The surgical incise drape of claim 1, wherein each rigid tab is positioned between the pressure-sensitive adhesive and the release liner.

16. The surgical incise drape of claim 1, wherein the drape comprises the release liner adhered to the pressure-sensitive adhesive opposite the extensible film.

17. The surgical incise drape of claim 1, wherein the extensible carrier is removably adhered such that it is removable in one piece after application of the drape to the patient.

18. The surgical incise drape of claim 1, wherein the pressure-sensitive adhesive is adhered to the entire first major surface of the extensible film.

19. The surgical incise drape of claim 1, wherein the pressure-sensitive adhesive is adhered to the first major surface of the extensible film at a point where a surgical incision is to be made on the patient's body.

20. The surgical incise drape of claim 1, wherein the extensible carrier is removably adhered across the entire second major surface of the extensible film.

21. The surgical incise drape of claim 1, wherein the extensible carrier is removably adhered to the extensible film essentially only along its perimeter.

* * * * *

UNITED STATES PATENT AND TRADEMARK OFFICE
CERTIFICATE OF CORRECTION

| | | |
|---|---|---|
| PATENT NO. | : 10,639,118 B2 | Page 1 of 1 |
| APPLICATION NO. | : 13/081021 | |
| DATED | : May 5, 2020 | |
| INVENTOR(S) | : McGuire, Jr. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 464 days.

Signed and Sealed this
Twenty-fourth Day of November, 2020

Andrei Iancu
*Director of the United States Patent and Trademark Office*